US009026247B2

(12) United States Patent
White et al.

(10) Patent No.: US 9,026,247 B2
(45) Date of Patent: May 5, 2015

(54) MOTION AND VIDEO CAPTURE FOR TRACKING AND EVALUATING ROBOTIC SURGERY AND ASSOCIATED SYSTEMS AND METHODS

(75) Inventors: Lee Woodruff White, Seattle, WA (US); Timothy Mariusz Kowalewski, Seattle, WA (US); Thomas S. Lendvay, Seattle, WA (US); Blake Hannaford, Seattle, WA (US)

(73) Assignee: University of Washington through its Center for Communication, Seattle, WA (US)

( * ) Notice: Subject to any disclaimer, the term of this patent is extended or adjusted under 35 U.S.C. 154(b) by 395 days.

(21) Appl. No.: 13/434,585

(22) Filed: Mar. 29, 2012

(65) Prior Publication Data

US 2012/0253360 A1    Oct. 4, 2012

Related U.S. Application Data

(60) Provisional application No. 61/469,495, filed on Mar. 30, 2011, provisional application No. 61/556,110, filed on Nov. 4, 2011.

(51) Int. Cl.
*G06F 19/00* (2011.01)
*A61B 19/00* (2006.01)

(52) U.S. Cl.
CPC ......... *A61B 19/5244* (2013.01); *A61B 19/2203* (2013.01); *A61B 2019/223* (2013.01); *A61B 2019/5248* (2013.01); *A61B 2019/5251* (2013.01); *A61B 2019/5259* (2013.01)

(58) Field of Classification Search
USPC ................ 700/245, 250, 253, 254, 258, 259; 318/568.11, 568.12, 568.13, 568.16, 318/568.2, 568.21
See application file for complete search history.

(56) References Cited

U.S. PATENT DOCUMENTS

| 5,797,849 | A | 8/1998 | Vesely |
| 5,800,179 | A | 9/1998 | Bailey |
| 6,019,725 | A | 2/2000 | Vesely |
| 6,246,898 | B1 | 6/2001 | Vesely et al. |
| 6,377,011 | B1 * | 4/2002 | Ben-Ur ........................ 318/566 |

(Continued)

FOREIGN PATENT DOCUMENTS

| WO | 0188825 A2 | 11/2001 |
| WO | 2010108128 A2 | 9/2010 |
| WO | WO 2011150257 A2 * | 12/2011 |

OTHER PUBLICATIONS

Sun et al., Design and Development of a Da Vinci Surgical System Simulator, 2007, IEEE, Proceedings of the 2007 IEEE International Conference on Mechatronics and Automation, Aug. 5-8, 2007, Harbin, China, pp. 1050-1055.*

*Primary Examiner* — Khoi Tran
*Assistant Examiner* — Jaime Figueroa
(74) *Attorney, Agent, or Firm* — Perkins Coie LLP (57) ABSTRACT

The present technology is directed to motion and video capture for tracking and evaluating robotic surgery. In one embodiment, the system includes at least one tracking device coupled to a remote surgical tool. The tracking device is configured to use one or more sensors to sense one or more physical variables such as movement and electrical contact. In some embodiments, the data from multiple individual sensors is synchronized, received, and stored by a digital information system. The digital information system is configured to analyze the data to objectively assess surgical skill.

24 Claims, 7 Drawing Sheets

(56) References Cited

U.S. PATENT DOCUMENTS

| | | |
|---|---|---|
| 7,408,439 B2 | 8/2008 | Wang et al. |
| 7,835,785 B2 | 11/2010 | Scully et al. |
| 2003/0232579 A1* | 12/2003 | Carlson, III .................... 451/41 |
| 2006/0161302 A1* | 7/2006 | Perry et al. .................... 700/245 |
| 2006/0209019 A1* | 9/2006 | Hu ................................ 345/156 |
| 2006/0258938 A1 | 11/2006 | Hoffman et al. |
| 2007/0038059 A1 | 2/2007 | Sheffer et al. |
| 2007/0172803 A1 | 7/2007 | Hannaford et al. |
| 2008/0262654 A1* | 10/2008 | Omori et al. ................... 700/245 |
| 2009/0036902 A1 | 2/2009 | DiMaio et al. |
| 2009/0088634 A1 | 4/2009 | Zhao et al. |
| 2009/0088773 A1 | 4/2009 | Zhao et al. |
| 2009/0088897 A1 | 4/2009 | Zhao et al. |
| 2009/0248036 A1 | 10/2009 | Hoffman et al. |
| 2009/0268015 A1 | 10/2009 | Scott et al. |
| 2010/0228249 A1 | 9/2010 | Mohr et al. |
| 2010/0285438 A1 | 11/2010 | Kesavadas et al. |
| 2011/0015648 A1 | 1/2011 | Alvarez et al. |
| 2011/0020779 A1* | 1/2011 | Hannaford et al. ........... 434/262 |
| 2011/0050852 A1 | 3/2011 | Lamprecht et al. |
| 2013/0295540 A1* | 11/2013 | Kesavadas et al. ........... 434/262 |
| 2014/0155910 A1 | 6/2014 | Hannaford et al. |

* cited by examiner

MOTION AND VIDEO CAPTURE FOR TRACKING AND EVALUATING ROBOTIC SURGERY AND ASSOCIATED SYSTEMS AND METHODS

CROSS-REFERENCE TO RELATED APPLICATION(S)

This application claims the benefit of U.S. Provisional Application No. 61/469,495, titled "SURGTRAK: MOTION AND VIDEO CAPTURE FOR TRACKING AND EVALUATING ROBOTIC SURGERY" filed Mar. 30, 2011, and U.S. Provisional Application No. 61/556,110, titled "SURGTRAK: MOTION AND VIDEO CAPTURE FOR TRACKING AND EVALUATING ROBOTIC SURGERY" filed Nov. 4, 2011, both of which are incorporated herein by reference in their entireties.

STATEMENT REGARDING FEDERALLY SPONSORED RESEARCH

This invention was made with government support under W81XWH-09-1-0714 awarded by the Department of Defense. The government has certain rights in the invention.

TECHNICAL FIELD

The technologies disclosed in the present application generally relate to robotic surgical systems and methods for tracking and evaluating robotic surgery.

BACKGROUND

Robotically-assisted surgery was developed to overcome certain limitations of minimally invasive surgery and enhance the capabilities of surgeons performing open surgery. In some types of robotic surgery, the surgeon uses a telemanipulator to control the surgical instruments. A telemanipulator is a remote manipulator that allows the surgeon to perform the normal movements associated with the surgery while the robotic arms carry out those movements using end-effectors and manipulators to perform the actual surgery on the patient. In computer-controlled robotic surgery systems, the surgeon uses a computer to control the robotic arms and its end-effectors.

Specialized surgical training is needed to operate robotic surgery systems. Training surgeons to safely and efficiently use robotic surgery systems is necessary in order to achieve positive patient outcomes, reduce delays in the operating room, and limit the time the patient spends under anesthesia. Current robotic surgical training methods, however, can be time consuming for both the trainer and the trainee. Further, it can be difficult to determine whether a surgeon has gained sufficient proficiency with robotic surgery techniques.

DETAILED DESCRIPTION

The present technology is directed to apparatuses, systems, and methods for motion and video capture for tracking and evaluating robotic surgery. In one embodiment, for example, the system can include at least one tracking device coupled to a remote surgical tool. The tracking device is configured to use one or more sensors to sense one or more physical variables such as movement and electrical contact of the tool. Information relating to these physical variables is transmitted as data via a wired or wireless transmission component. In some embodiments, the data from multiple individual sensors is received, stored, and synchronized by a digital information system. The digital information system can also analyze the data to objectively assess surgical skill.

Specific details of several embodiments of the technology are described below with reference to FIGS. 1-7B. Although many of the embodiments are described below with respect to devices, systems, and methods for tracking and evaluation of robotic surgery, other applications and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1-7B.

Figure 1:
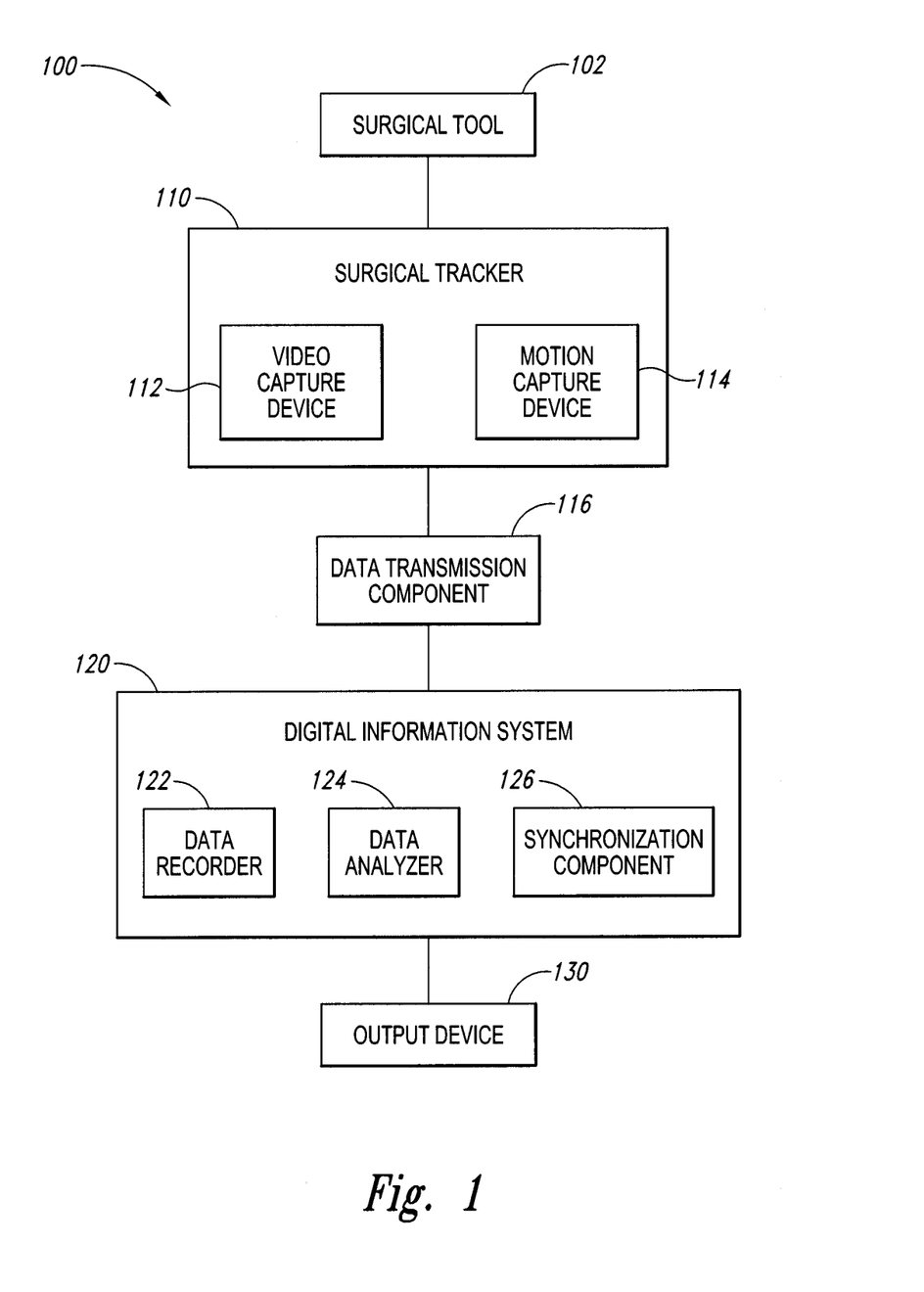
FIG. 1 is a schematic depiction of a robotic surgical system for tracking and evaluating robotic surgery in accordance with embodiments of the technology.

FIG. 1 is a schematic depiction of a robotic surgical system 100 for tracking and evaluating robotic surgery in accordance with embodiments of the present technology. The system 100 includes a modification device such as a tracker, e.g., a surgical tracker 110, coupled to a tool such as a surgical tool 102. In several embodiments, the surgical tool 102 can be any type of robotic surgical tool, such as surgical tools that are part of the da Vinci® Surgical System made by Intuitive Surgical of Sunnyvale, Calif. It will be appreciated that the system 100 may be used with a variety of different modification devices and/or tools. Further, in other embodiments, the system 100 may be used with other suitable surgical systems. The surgical tool 102 may be operated by direct telemanipulation, computer control, or other suitable means.

The surgical tracker 110 can detect, measure, or otherwise capture information associated with one or more physical variables. In a particular embodiment, the surgical tracker 100 captures video and motion data relating to the surgical tool 102 using a video capture device 112 and a motion capture device 114, respectively. As will be described in further detail below, the motion capture device 114 can capture positional state information (e.g., absolute and relative position, orientation, velocity, acceleration, and jerk in both linear and angular coordinates) and electrical contact information for the surgical tool 102.

The data can further include an input or output of a user (or users) using the surgical tool 102. Examples of inputs include a visual stimulus provided to the user, a haptic stimulus, a tactile stimulus, an object temperature, an environmental temperature, an olfactory stimulus, an auditory stimulus, a gustatory stimulus, a magnetic field, an electric field, a chemical stimulus, etc. Examples of user outputs include a movement, stress, torque, or other force, a computer command, etc. The data can be captured by various types of sensing devices, such as a potentiometer, an optical encoder, a Hall effect sensor, a linear transducer, electromagnetic tracking, a visual means, an ultrasonic means, a laser, an X-ray, a global positioning system, a local positioning system, a structured light means, a physically connected tracking means, a force sensor, a strain gauge (e.g., a Bragg sensor), deformation and visual sensing, a direct voltage signal sensor, a combination of these means, or other means. It will be appreciated that the inputs, outputs, and sensing devices described above are merely provided as examples, and in other embodiments other types of inputs, outputs, and/or sensing devices may be used.

The video capture device 112 is configured to capture video data with a camera coupled to the surgical tracker 110, the surgical tool 102, a secondary surgical tool, or other parts of the robotic surgical system 100 (e.g., coupled to an endoscope, not shown), or it can be remotely positioned. In some embodiments, video data is captured by using at least one of a three-dimensional video recording system, structured infrared light, time of flight light, a fusion of multiple camera views, two-camera stereoscopy, or a combination thereof. In further embodiments, the video capture device 112 can record a video stream presented to the user of the surgical tool 102. For example, the user can view a screen that indicates when a camera, tool-activating clutch, or other system component has been triggered. This stream can be recorded to provide context for other data captured by the system 100. In several embodiments, the data is detected separately from any data collected by the surgical tool 102 itself. The video capture device 112 can accordingly capture additional data or events that are not otherwise directly measured or recorded (e.g., by the motion capture device 114). In selected embodiments, the video capture device 112 can capture one or more streams of high resolution video (e.g., around 30 frames per second and 1080 lines of vertical resolution).

The data captured by the video capture device 112 and the motion capture device 114 can be transmitted to a digital information system 120 via a wired or wireless data transmission component 116, or a combination thereof. In some embodiments, for example, the data transmission component 116 is configured to transmit a detected input or output as at least one of a digital, analog, light, fiber optic, or radio frequency signal, or a combination of these or other signals. In a particular embodiment, the data transmission component 116 comprises a multi-channel data bus having both wired and wireless transmission components. In some embodiments, the data transmission component 116 is configured to convert a digital signal to an analog signal (or vice versa) before transmission. In some embodiments, the data transmission component 116 is configured to transmit data to an intermediate data acquisition device as part of the transmission. In still other embodiments, the data transmission component 116 may have other configurations and/or features.

The digital information system 120 can include a data recorder 122, a synchronization component 126, and a data analyzer 124. The data recorder 122 is configured to record and store the video and motion/positional data described above, electrical contact data, user data, and other types of data. In some embodiments, for example, the data recorder 122 can record data from multiple sources, e.g., multiple data streams such as time series data. The data recorder 122 may also be configured to store the multiple data streams in memory concurrently. In some embodiments, for example, positional data can be recorded and time stamped. The memory can be coupled to the surgical tracker 110, the digital information system 120, a remote computer system, a network of multiple connected computers, and/or other component of the system 100. The data recorder 122 can store the data as a single unified data structure, a set of computer files, a video file, a text file, a file in a custom format, a file in a binary format, or a combination thereof.

The synchronization component 126 is configured to sync various types of data (e.g., data from multiple sources) and/or sync data based on a common reference point (e.g., time-sync video and motion data). In various embodiments, the synchronization component 126 can comprise a system timer running on a remote computer system, markers in multiple files associated with the data from multiple sources, and/or simultaneous initiation of recording to multiple files. As will be described in further detail below, in further embodiments the synchronization component 126 can associate the data with a unique serial number associated with the particular surgical tool 102 and broadcasted by a chip on the surgical tracker 110.

The data analyzer 124 is configured to implement mathematical models to transform the recorded data into a more useful format. In some embodiments, for example, the data analyzer 124 can implement mathematical models to compensate for sensor/measurement errors. For example, the data analyzer 124 can implement a mathematical model to compensate for kinematic or dynamic errors in the measured operations of the surgical tool 102. A kinematic model can compensate for coupling between axes of motion of the surgical tool 102. A dynamic model can compensate estimates of the surgical tool 102 position for elasticity of mechanical or virtual transmission. In still further embodiments, the mathematical model is a data driven model, a Kalman filter, or a combination of these or other models. The data analyzer 124 can further include means configured to improve the synchronization of the data, such as producing a comparison of video data and movement data by rendering tool movements in a virtual three-dimensional environment.

The data analyzer 124 may be further configured to implement statistical models to compare signals obtained from the surgical tracker 110 with signals obtained from experienced users. For example, the quantity, direction, duration, pattern, force, path length, or sequence of surgical tool 102 movement can be evaluated against a preferred or ideal set of operations. In a further embodiment, the data can be used to estimate tissue stress based on the movement or operation of the surgical tool and compare the estimated tissue stress to a known preferred limit of tissue stress as a way to evaluate a user's skill. In some embodiments, the data analyzer 124 can generate a performance indicator based on the comparison. In further embodiments, the data analyzer can compare a user's performance against a previous performance, to indicate whether there has been skill or proficiency improvement. In still further embodiments, the data analyzer 124 can assess the user's skill by evaluating the ability of the user to process inputs and choose a preferred output. As will be discussed in further detail below, the data analyzer 124 may provide additional feedback to the user or to an evaluator to guide and improve the user's performance.

In various embodiments, the computing devices on which the digital information system 120 is implemented may include a central processing unit, memory, input devices (e.g., keyboard and pointing devices), output devices 130 (e.g., display devices), and storage devices (e.g., disk drives). The memory and storage devices are computer-readable media that may be encoded with computer-executable instructions. In addition, the instructions, data structures, and message structures may be stored or transmitted via the data transmission medium 116, such as a signal on a communications link and may be encrypted. Various communications links may be used, such as the Internet, a local area network, a wide area network, a point-to-point dial-up connection, a cell phone network, and so on. Data may also be transmitted as files stored on a portable data storage medium. In some embodiments, the digital information system 120 can include a number of programming libraries to enable network-based communication with data sources, data recording systems, etc.

Embodiments of the digital information system 120 may be implemented and used with various operating environments that include personal computers, server computers, handheld or laptop devices, multiprocessor systems, microprocessor-based systems, programmable consumer electronics, digital cameras, network PCs, minicomputers, mainframe computers, computing environments that include any of the above systems or devices, and so on.

The digital information system 120 may be described in the general context of computer-executable instructions, such as program modules, executed by one or more computers or other devices. Generally, program modules include routines, programs, objects, components, data structures, and so on that perform particular tasks or implement particular abstract data types. Typically, the functionality of the program modules may be combined or distributed as desired in various embodiments. In some embodiments, the digital information system 120 can include databases for detected or predetermined data, such as surgical tool parameters or calibration data associated with the surgical tool 102.

The output device 130 is configured to display or otherwise convey to a user the data or an analysis of the data captured by the surgical tracker 110. For example, the output device 130 may display a chart or graph indicating the performance of the user of the surgical tool 102, either alone or compared against a control or an experienced user (see, e.g., FIGS. 7A and 7B, discussed below). In some embodiments, the output device 130 can include a reconstruction component configured to reconstruct a three-dimensional rendering of an operation of a user-controlled system in a virtual environment. Such output is expected to enable users to reduce training time, maximize surgery skills, and improve surgical outcomes. In further embodiments, feedback to the user may include a stimulus intended to trigger a user response, such as a haptic stimulus, a tactile stimulus, an object temperature, an environmental temperature, an olfactory stimulus, an auditory stimulus, a gustatory stimulus, a magnetic field, an electric field, a chemical stimulus, or any other stimulus perceptible to the user. In various situations, the user may be a trainee, a trainer, a proctor, or other user.

Figure 2A:
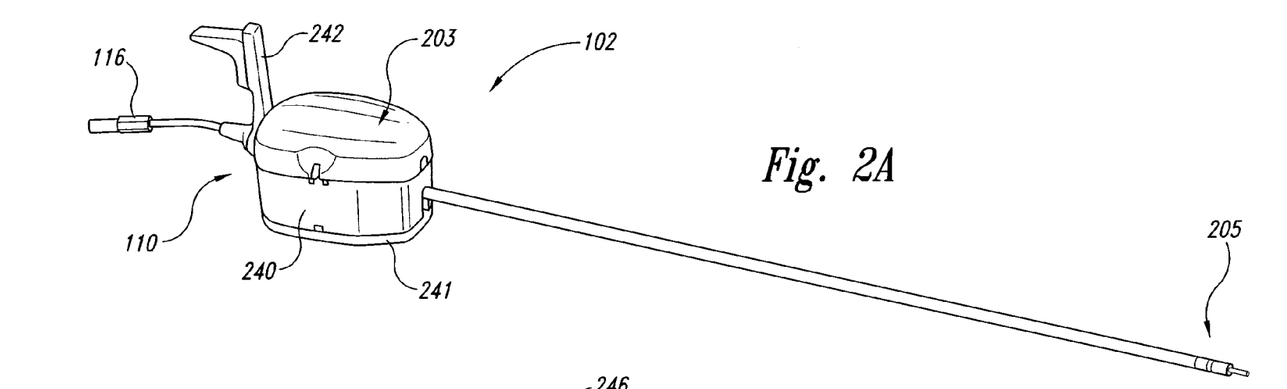
FIG. 2A is an isometric view of a surgical tracker coupled to a surgical tool in accordance with embodiments of the technology.

FIG. 2A is an isometric view of the surgical tracker 110 coupled to the surgical tool 102 in accordance with embodiments of the technology. The surgical tool 102 can have a proximal portion 203 and a distal portion 205, and be driven by a driving apparatus, such as a rotating spindle, prismatic joint, or the like (see, for example, spindles 384 depicted in FIG. 3 below). As will be described in further detail below with reference to FIG. 4, the surgical tool 102 may also include a distal end effector, such as a needle driver or other mechanical component. The driving apparatus can transmit motion via a mechanical or virtual linkage to the end effector, or multiple mechanical or virtual linkages running in series or parallel. In some embodiments, the end effector is driven by at least one of a pneumatic means, a hydraulic means, an electromagnetic means, a mechanical linkage, or a combination thereof.

Figure 2B:
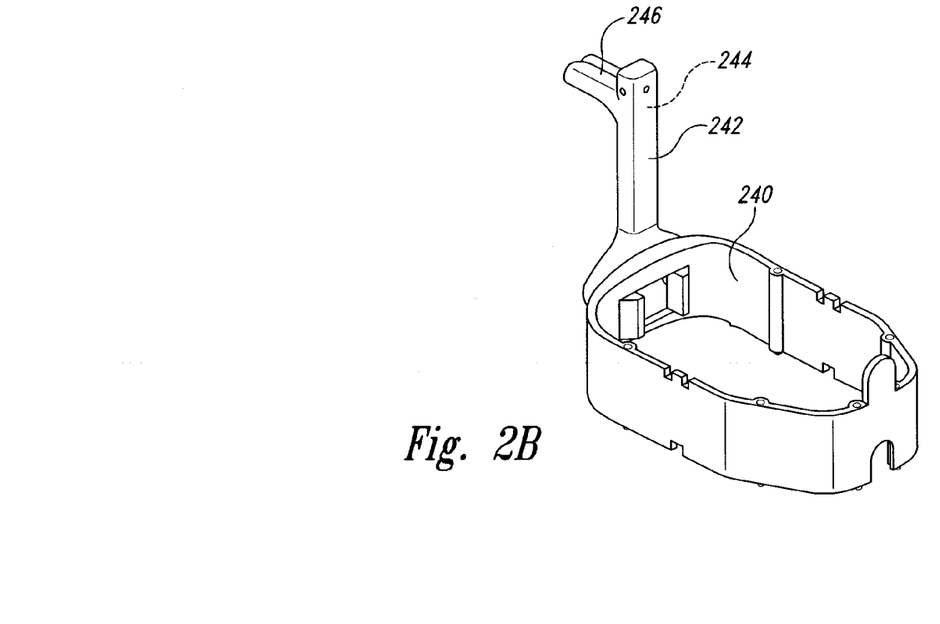
FIG. 2B is an isometric view of a base portion of the surgical tracker shown in FIG. 2A in accordance with embodiments of the technology.
Figure 3:
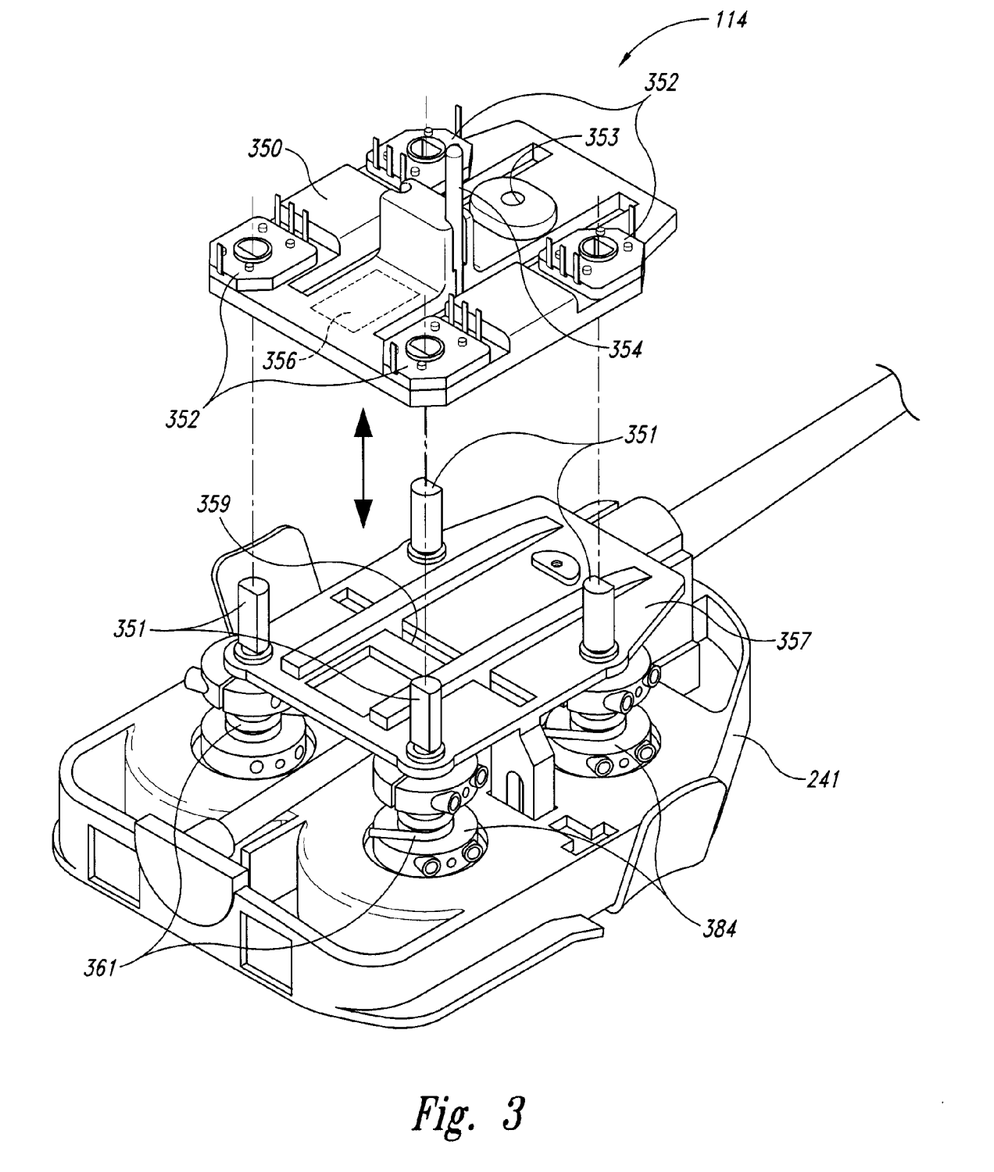
FIG. 3 is a partially schematic isometric view of a portion of a motion capture device coupling to a portion of a surgical tool configured in accordance with embodiments of the technology.
Figure 4:
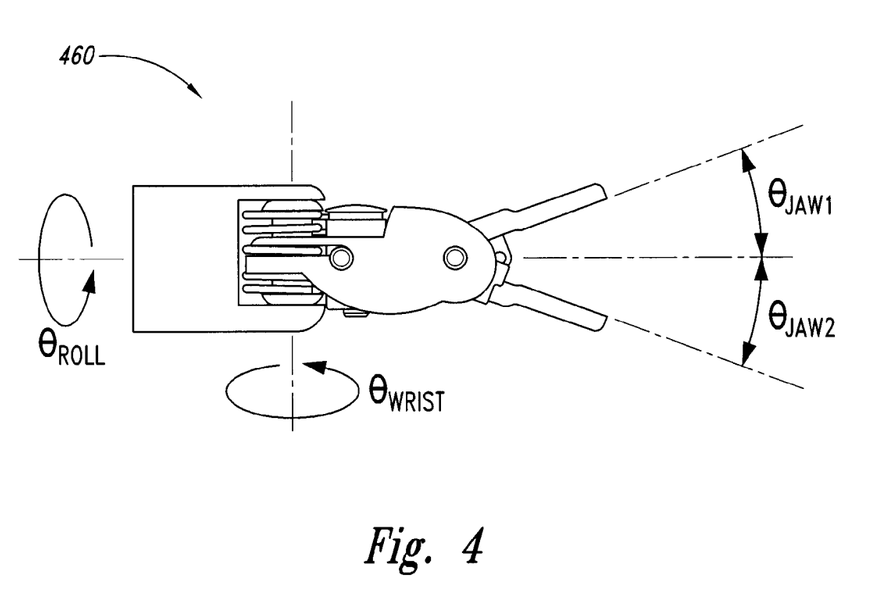
FIG. 4 is a top view of a surgical tool configured in accordance with embodiments of the technology.

The surgical tracker 110 can include a base portion 240 configured to couple the motion capture device 114 to a portion of the surgical tool 102 housed in a surgical tool support portion 241. To provide further clarity, FIG. 2B illustrates the base portion 240 detached from the surgical tool 102 and FIG. 3 illustrates an internal view of the surgical tool support portion 241 and motion capture device 114. Referring to FIGS. 2A and 2B together, the base portion 240 and surgical tool support portion 241 can house all or a portion of the motion capture device 114 and/or the video capture device 112 (shown schematically in FIG. 1). The base portion 240 includes an electromagnetic tracker housing 242 extending upward from a proximal portion of the base portion 240. The electromagnetic tracker housing 242 can encase or at least partially surround an electromagnetic tracker 244 of the motion capture device 114. The functionality of the electromagnetic tracker 244 will be described in further detail below with reference to FIG. 3.

The base portion 240 is configured to be attached to the surgical tool support portion 241 by screwing, friction fit, latching, clipping, fastening, gluing, soldering, welding, brazing, press fitting, or other suitable attachment techniques. In some embodiments, the base portion 240, surgical tool support portion 241, and/or other portions of the surgical tool 102 may be made of sterilizable materials suitable for use in a surgical field.

As described above, in several embodiments the data transmission component 116 can comprise one or more wires extending from the surgical tracker 110 to the digital information system 120 (shown schematically in FIG. 1). In the embodiment illustrated in FIG. 2A, for example, the data transmission component 116 comprises a wire-containing cable extending from a stress-relief component 246 extending proximally outward from the tracker housing 242. The stress-relief component 246 can direct the cable toward the digital information system 120 and away from the surgical field, and can also relieve stress on the cable by inhibiting excessive bending or twisting of the cable during manipulation of the surgical tool 102. In other embodiments, however, the data transmission component 116 may have a different arrangement and/or features.

FIG. 3 is a partially schematic isometric view of a portion of the motion capture device 114 coupling to a portion of the surgical tool 102 housed in the surgical tool support portion 241 in accordance with embodiments of the technology. The motion capture device 114 comprises a combination of the electromagnetic tracker 244 (shown in FIG. 2B) and a plurality of potentiometers 352 positioned on a plate 350 that is sized to interface with a corresponding receiving plate 357 on the surgical tool 102. The electromagnetic tracker 244 is configured to sense field intensity and provide position/orientation data for the surgical tool 102, while the potentiometers 352 act as angle transducers to provide data related to the pose of the surgical tool 102 (e.g., the surgeon's hand motion with respect to the patient). The potentiometers 352 can be coupled to the plate 350 with a flexible adhesive, such as silicon glue, or with other attachment mechanisms. In the illustrated embodiment, the individual potentiometers 352 are aligned with the plate 350 and the surgical tool 102 with interface pins 351. The interface pins 351 can run from the surgical tool 102 driving apparatus (e.g., spindles 384), through the receiving plate 357 and the motion capture device plate 350, and couple to the potentiometers 352. In the illustrated embodiment, the interface pins 351 have a D-shaped cross-section, but can have other shapes in other embodiments. In some embodiments, the plate 350 is plastic or partially plastic and is coupled to the receiving plate 357 on the surgical tool 102 with a screw (e.g., through a screw-hole 353) or other fastening mechanism (e.g., adhesive). The plate 350 can be spaced apart from the surgical tool 102 within the base 240. In other embodiments, the potentiometers 352 and/or the plate 350 may have different features and/or a different arrangement relative to each other. The calibration of the potentiometers 352 will be described below with reference to FIGS. 5A and 5B.

The electromagnetic tracker 244 works by measuring the position (i.e., x, y, and z coordinates), and the orientation (i.e., yaw, pitch, and roll) of the surgical tool 102 with respect to a reference point. The electromagnetic tracker 244 generates a signal that indicates these positioning coordinates and sends this signal to be received/processed by the digital information system 120 in the manner described above. In various embodiments, the signal can comprise a digital, analog, light, fiber optic, or radio frequency signal, or a combination of these and other signals. The calibration of the electromagnetic tracker 244 will be described below with reference to FIG. 6.

The potentiometers 352 are configured to detect tool tip position of the surgical tool 102. For example, the potentiometers 352 can measure the spindle angles of a surgical tool such as a large needle driver 460 shown in FIG. 4. The needle driver 460 is driven by four spindles (not shown) in the tool body that drive the four tool degrees of freedom (the spindle angles are individually identified as $\theta_{roll}$, $\theta_{wrist}$, $\theta_{jaw1}$, and $\theta_{jaw2}$). By measuring the voltage of the potentiometers associated with these individual angles, the variation from a baseline position can be ascertained and recorded. This data translates into a reading of the position of the needle driver 460 at a given moment.

Referring back to FIG. 3, the motion capture device 114 further includes an electrical contact sensor 354 for establishing electrical conductivity with the distal portion 205 of the surgical tool 102. In several embodiments, for example, an electrical connection runs through the surgical tool 102 from the tool tip at the distal portion 205 to the proximal portion 203 (see the distal and proximal portions 205, 203 in FIG. 2A). The electrical contact sensor 354 can be a metallic component (e.g., gold) that is in electrical communication with a metallic component at the distal portion 205. The electrical contact sensor 354 can penetrate the receiving plate 357 at a through hole 359 to reach the distal portion 205 of the surgical tool 102. The through hole 359 can be integral to the surgical tool 102 or can be added to the surgical tool 102 by drilling or another suitable method to accommodate the electrical contact sensor 354. In some embodiments, the individual interface pins 351 and corresponding spindles 384 can be electrically connected to the electrical contact sensor 354 with conductive guide cables 361. In some embodiments, the electrical contact sensor 354 is spring-loaded to ensure sufficient electrical contact with a metallic component of the surgical tool 102. In several embodiments, the surgical task uses electrically conductive components of the surgical tool 102, and these electrically conductive components are connected to a common ground with the electrical contact sensor 354. The digital information system 120 can thereby register, record, or transmit the contact between the surgical tool 102 with grounded surgical task elements. Variables within a surgical environment (e.g., temperature, pH, immunohistochemistry, electrical impedance, physical impedance, an optical characteristic, tissue contact, transmissibility of radiation, an electromagnetic characteristic, etc.) can likewise be detected by registering this contact and the system can thereby register if an improper surface has been contacted by the surgical tool 102 or determine the physiologic state of the tissue in contact.

In some embodiments, the plate 350 can further include a microprocessor 356 that broadcasts a unique identifier associated with the remotely controlled tool. The unique identifier, for example, can be a serial number that encodes information specific to the remotely controlled tool. This unique information can provide more specific data to the digital information system 120 for a more customized data analysis. For example, the digital information system 120 can reference calibration parameters specific to the tracked surgical tool 102 based on the unique identifier. In some embodiments, the broadcast may be adapted to be readable by the data recorder 122.

In addition to tool-specific information, the digital information system 120 can record user-specific information. Some types of user data that can be sensed and recorded about an operator of the surgical tool 102 include: a physiologic sign such as at least one of respiration, heart rate, an electrocardiographic signal, an odor, or a user skin color; an electromyographic sign; a neurologic sign; an electroencephalographic signal; an electrocorticographic signal; a peripheral nervous system activity; user motion (e.g., a hand motion); a force produced by the user; a motion or force produced by the user in interacting with the surgical tool; a vocalization; eye movement; bilateral pupil size; hemoglobin saturation; galvanic skin response; blood chemistry; a functional magnetic resonance image (MRI); brain activity; a thought; a voluntarily conveyed dialog; a stream of consciousness; or a combination thereof. This data can be captured by appropriate sensors, e.g., an MRI, a pupil size indicator, a body temperature thermometer, etc., and provided to the digital information system 120.

Figure 5A:
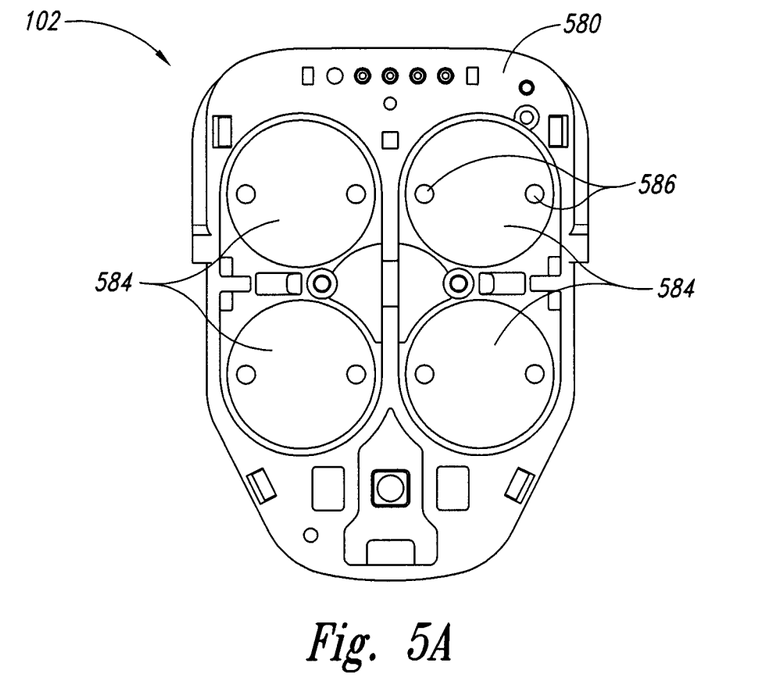
FIGS. 5A and 5B are components of a potentiometer calibration system configured in accordance with embodiments of the technology.
Figure 5B:
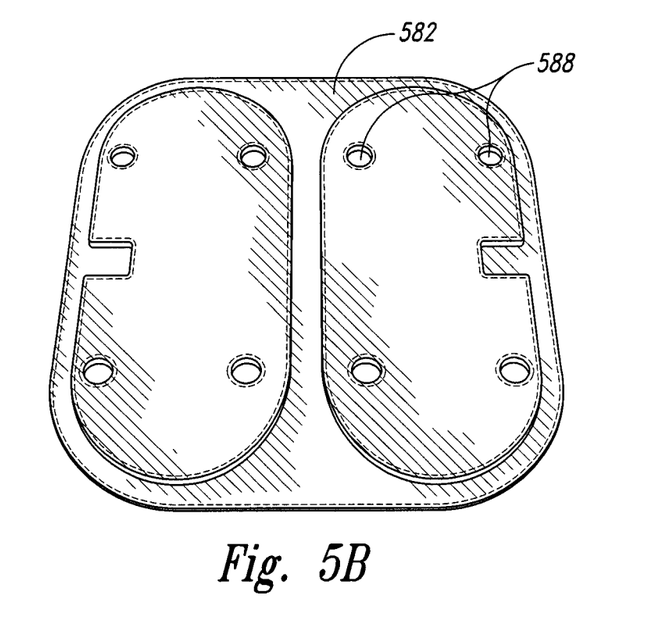

FIGS. 5A and 5B are components of a potentiometer calibration system configured in accordance with embodiments of the technology. FIG. 5A illustrates an undersurface 580 of the proximal portion 203 of the surgical tool 102. FIG. 5B illustrates a calibration plate 582 configured to interface with the undersurface 580 of the surgical tool 102. Referring to FIGS. 5A and 5B together, protrusions 586 in rotatable spindles 584 on the undersurface 580 correspond to matching recesses 588 in the calibration plate 582. The protrusions 586 can be aligned and pressed into the recesses 588. By fixing the surgical tool 102 in a particular, known orientation corresponding to the orientation of the recesses 588 in the calibration plate 582, a baseline can be established for any spindle angle deviation from this orientation. For example, when aligned with the calibration plate 582, the four spindle angles can be considered to be zero degrees. At this same time, the pose of the distal portion 205 of the surgical tool 102 may be measured and the correspondence between spindle angle and tool pose can be determined. When the surgical tool 102 is later manipulated by the user, the spindle angles $\theta_{roll}$, $\theta_{wrist}$, $\theta_{jaw1}$, and $\theta_{jaw2}$ will deviate from the zero angle. A voltage reading of the potentiometers can be taken that indicates this deviation, and the surgical tool 102's tip pose can be determined. The illustrated undersurface 580 and calibration plate 582 show just one combination of a surgical tool design and corresponding calibration plate. In further embodiments where the surgical tool 102 has an alternative undersurface design, a corresponding alternate calibration plate can be used. In still other embodiments, other suitable techniques may be used to calibrate the potentiometers.

Figure 6:
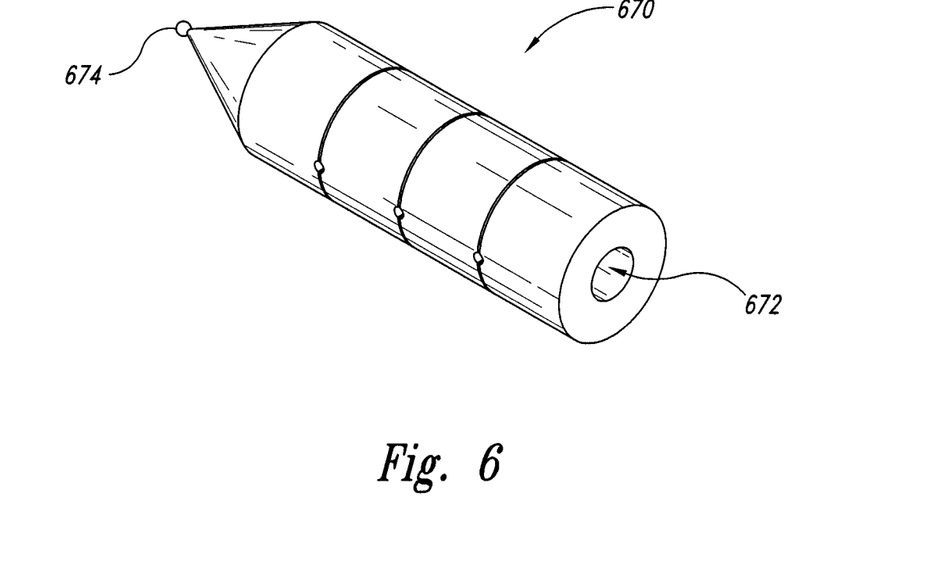
FIG. 6 is a component of an electromagnetic calibration system configured in accordance with embodiments of the technology.

FIG. 6 is a component of an electromagnetic calibration system configured in accordance with embodiments of the technology. More specifically FIG. 6 illustrates a tip registration sleeve 670 having a spherical tip 674. The sleeve 670 comprises an internal lumen 672 that matches an outside diameter of the surgical tool 102 (FIG. 2A). In various embodiments, the lumen 572 can be adapted to fit a variety of tool diameters and shapes. In operation, at least a portion of the surgical tool 102 can be inserted into the lumen 672 and sequentially fixed to multiple internal depths, placing the spherical tip 674 at known offsets from a point of interest (e.g., a distal tip or a point coincident with a axis of rotation of the distal portion 205) on the surgical tool 102. The spherical tip 674 can be fixed to a spherical socket (not shown) while the surgical tracker 110 is moved to predetermined positions (e.g., three predetermined points on a spherical form) or a multitude of non-predetermined positions to produce a set of position data. From this set of points, a spherical regression algorithm can estimate the location of the spherical tip 674 as a control point, and the location of the surgical tool 102 can then be determined with reference to this control point. As described above, the electromagnetic tracker 244 (shown in FIG. 2B) can send a signal of its location with reference to this control point. In other embodiments, the electromagnetic calibration system may have different Features and/or include a different configuration.

Figure 7A:
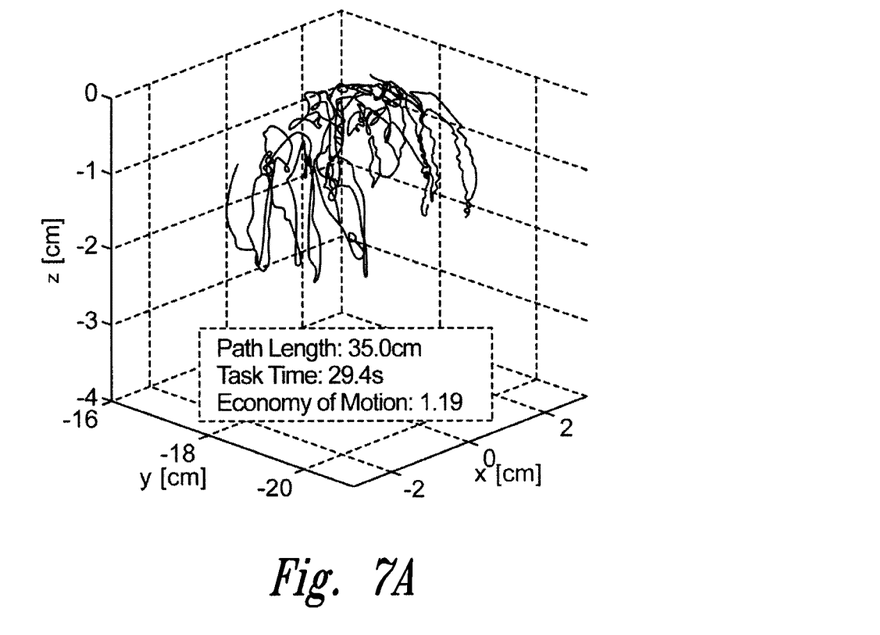
FIGS. 7A and 7B are graphs illustrating data captured by a surgical tracker in accordance with embodiments of the technology.
Figure 7B:
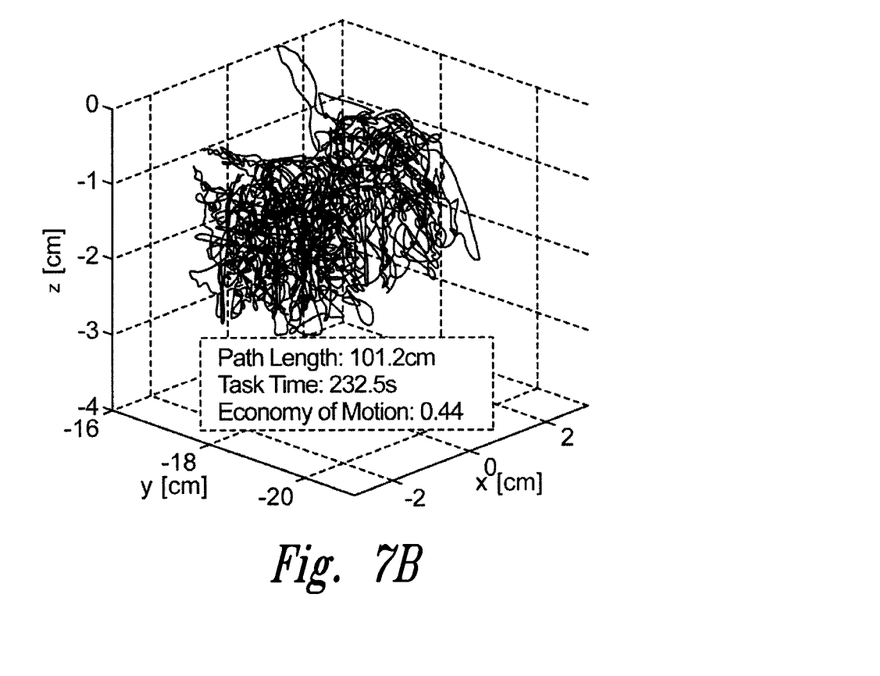

FIGS. 7A and 7B are graphs illustrating an example dataset captured by the surgical tracker 110 in accordance with embodiments of the technology. More specifically, FIG. 7A is a graph illustrating a tool path of an expert surgical operator and FIG. 7B is a graph illustrating a tool path of a novice operator. Datasets such as these can be obtained from a user performing a procedure or set of tasks using the surgical tool 102 having the surgical tracker 110 attached. The surgical tracker 110 captures video and positional data in the manner described above. Data is sent to the digital information system 120 to be recorded, synced, and analyzed.

In the illustrated embodiments, the data has been converted to 3-dimensional renderings of the tool paths of the users and can be displayed on the output device 130. Mathematical operations have been performed to calculate statistics such as path length, task time, and economy of motion. For example, using calibration data, tool tip position is determined by first calculating a control point in the manner described above and then tool tip location is determined from spindle data. The statistics and the tool path rendering from the novice are compared to those of the expert performing the same tasks to objectively assess skill and improve training. From the rendering, it is apparent that the novice user made significantly more tool motions with an overall greater path length.

More detailed analyses can be performed using the data. For example, the data can be broken down into task-specific assessments, and the time or path length for individual tasks can be analyzed. Some example tasks can include suturing, transferring a block from one location to another, transferring a group of rings from one tower to another, etc., or practicing surgical tasks on an animal or anatomical model. The digital information system 120 can further record and track skill level over several trials and indicate whether there has been improvement. In some embodiments, a novice could be deemed to have sufficient proficiency when their metrics are within a certain percentage (e.g., 80%) of an experienced user over repeated trials. Technical and cognitive errors (e.g., unacceptable tissue contact) can be recorded.

From the foregoing, it will be appreciated that specific embodiments of the technology have been described herein for purposes of illustration, but that various modifications may be made without deviating from the spirit and scope of the disclosure. For example, structures and/or processes described in the context of particular embodiments may be combined or eliminated in other embodiments. Further, system components such as the motion capture device, video capture device, or other components can be coupled to parts of the surgical system other than those described above. For example, the motion capture device and/or video capture device could be attached to a sterile barrier between the user and the surgical tool, or could be attached to an arm portion of a surgical robot controlling the surgical tool. Moreover, while advantages associated with certain embodiments of the technology have been described in the context of these embodiments, other embodiments may also exhibit such advantages, and not all embodiments need necessarily exhibit such advantages to fall within the scope of the technology.

We claim:

1. A system for tracking performance of a remotely controlled tool, the system comprising:
   a modification device coupled to the remotely controlled tool, wherein the modification device comprises a motion capture device having sensors at a first location configured to sense one or more physical variables associated with use of the remotely controlled tool, the physical variables including position and orientation data of at least one joint of the remotely controlled tool at a second location away from the first location, and further wherein the modification device uses multiple recordings to sense the one or more physical variables;
   a data transmission component operably coupled to the modification device and configured to transmit data, wherein the data includes information associated with the one or more physical variables;
   a synchronization component configured to synchronize the multiple recordings; and
   a digital information system configured to receive and store the transmitted data.

2. The system of claim 1 wherein:
   the at least one joint includes at least one rotating spindle;
   the remotely controlled tool comprises an end effector configured to perform a surgical function; and
   the end effector is driven by the at least one rotating spindle.

3. The system of claim 2 wherein the modification device is configured to sense rotation of the at least one spindle.

4. The system of claim 3 wherein the modification device is configured to sense rotation of the at least one spindle with at least one of potentiometers, optical encoders, Hall effect sensors, or a combination thereof.

5. The system of claim 2 wherein the digital information system is configured to compute motion of the end effector.

6. The system of claim 1 wherein the motion capture device is configured to transmit a signal corresponding to the position and orientation of the remotely controlled tool with respect to a reference point.

7. The system of claim 1 wherein the modification device includes a digital device configured to broadcast a unique serial number associated with the remotely controlled tool.

8. The system of claim 1 wherein the modification device comprises a video capture device configured to record video being output to a user, and wherein the digital information system is configured to receive and store the recorded video.

9. The system of claim 1 wherein the modification device comprises an electrical contact sensor configured to transmit a signal relating to at least one of temperature, pH, immunohistochemistry, electrical impedance, physical impedance, an optical characteristic, tissue contact, transmissibility of radiation, or an electromagnetic characteristic.

10. A system for tracking performance of a robotic surgical tool, the system comprising:
- a surgical tracker configured to be removably coupled to the surgical tool at a first location, the surgical tracker comprising a video capture device configured to capture video of the surgical tool and a motion capture device configured to sense the position of at least one joint of the surgical tool at a second location spaced apart from the location;
- a data transmission component configured to transmit video and position data captured by the video capture device and the motion capture device, respectively; and
- a digital information system configured to receive and store the transmitted video and position data, wherein the digital information system comprises a data recorder, a synchronization component, and a data analyzer.

11. The system of claim 10 wherein:
the at least one joint includes at least one rotating spindle;
the robotic surgical tool comprises an end effector;
the end effector is driven by the at least one rotating spindle; and
the motion capture device is configured to sense rotation of the at least one spindle.

12. The system of claim 11 wherein the end effector is driven by a plurality of rotating spindles, and wherein the motion capture device comprises a plurality of potentiometers, each potentiometer configured to sense rotation of an individual spindle.

13. The system of claim 10 wherein the motion capture device comprises an electromagnetic tracker configured to transmit a signal corresponding to the position and orientation of the robotic surgical tool with respect to a static reference point.

14. The system of claim 10 wherein the surgical tracker comprises a digital device configured to broadcast a unique serial number associated with the robotic surgical tool.

15. The system of claim 10 wherein the synchronization component is configured to time-sync data provided by the video capture device with data provided by the motion capture device.

16. The system of claim 10 wherein the synchronization component is configured to time-sync data provided by the video capture device and data provided by the motion capture device with data from an additional source.

17. The system of claim 10 wherein the surgical tracker comprises an electrical contact sensor configured to transmit a signal relating to at least one of temperature, pH, immunohistochemistry, electrical impedance, physical impedance, an optical characteristic, tissue contact, transmissibility of radiation, an electromagnetic characteristic.

18. The system of claim 10 wherein the data analyzer is configured to compute a performance indicator based on at least one of the quantity, direction, duration, pattern, force, path length, or sequence of movement of the robotic surgical tool.

19. The system of claim 10, further comprising:
- a plurality of potentiometers, each potentiometer configured to sense rotation of an individual joint driving the robotic surgical tool, wherein the joint includes at least one rotating spindle;
- an electromagnetic tracker configured to transmit a signal corresponding to the position and orientation of the robotic surgical tool with respect to a static reference point;
- a digital device configured to broadcast a unique serial number associated with the robotic surgical tool;
- an electrical contact sensor configured to transmit a signal relating to at least one of temperature, pH, immunohistochemistry, electrical impedance, physical impedance, an optical characteristic, tissue contact, transmissibility of radiation, an electromagnetic characteristic; and
- an output device configured to output a performance indicator based on at least one of the quantity, direction, duration, pattern, force, path length, or sequence of movement of the robotic surgical tool.

20. The system of claim 7 wherein the digital information system is configured to reference calibration parameters specific to the remotely controlled tool based, at least in part, on a unique serial number associated with the remotely controlled tool.

21. The system of claim 1 wherein the digital information system is configured to analyze and determine position and orientation of components of the remotely controlled tool using a combination of recordings from at least one potentiometer and at least one electromagnetic tracker of the modification device.

22. The system of claim 1 wherein the digital information system is configured to simultaneously record and synchronize data of the remotely controlled tool and physiological data associated with a user of the tracking system.

23. The system of claim 1, further comprising a potentiometer calibration system configured to fix the remotely controlled tool in a baseline orientation corresponding with at least one recess of a calibration plate, and wherein:
the calibration plate is configured to interface with a proximal portion of the remotely controlled tool, and
the proximal portion of the remotely controlled tool includes at least one spindle comprising at least one protrusion configured to align with the at least one recess of the calibration plate.

24. The system of claim 1, further comprising an electromagnetic calibration system configured to determine the location of a tip of the remotely controlled tool with respect to a reference point, wherein the electromagnetic calibration system comprises a tip registration sleeve defining an internal lumen that corresponds with an outside diameter of the remotely controlled surgical tool.

* * * * *